(12) United States Patent
Millar (10) Patent No.: US 11,067,524 B2
(45) Date of Patent: Jul. 20, 2021

(54) SYSTEMS AND METHODS FOR TESTING FOR CONTAMINANTS IN AN ASSEMBLY LINE GROW POD

(71) Applicant: Grow Solutions Tech LLC, Lehi, UT (US)

(72) Inventor: Gary Bret Millar, Highland, UT (US)

(73) Assignee: Grow Solutions Tech LLC, Vineyard, UT (US)

( * ) Notice: Subject to any disclaimer, the term of this patent is extended or adjusted under 35 U.S.C. 154(b) by 447 days.

(21) Appl. No.: 15/977,399

(22) Filed: May 11, 2018

(65) Prior Publication Data

US 2018/0364187 A1    Dec. 20, 2018

Related U.S. Application Data

(60) Provisional application No. 62/519,403, filed on Jun. 14, 2017.

(51) Int. Cl.
*A01G 9/14* (2006.01)
*A01G 9/08* (2006.01)
(Continued)

(52) U.S. Cl.
CPC .............. *G01N 27/06* (2013.01); *A01G 9/085* (2013.01); *A01G 9/143* (2013.01); *A01G 25/16* (2013.01);
(Continued)

(58) Field of Classification Search
CPC ...... A01G 31/04; A01G 31/042; A01G 25/16; A01G 25/167; A01G 9/143
See application file for complete search history.

(56) References Cited

U.S. PATENT DOCUMENTS 5,088,231 A    2/1992  Kertz
8,836,504 B2   9/2014  Köhler
(Continued)

FOREIGN PATENT DOCUMENTS

EP    2166347 A1    3/2010
GB    2121263 A     12/1983
(Continued)

OTHER PUBLICATIONS

Jonathan West, Christy Charlton, Kelsey Kaplan, Conductivity Meters, Feb. 15, 2017, Encyclopedia of Chemical Engineering (Year: 2017).*
(Continued)

*Primary Examiner* — Magdalena Topolski
*Assistant Examiner* — Katelyn T Truong
(74) *Attorney, Agent, or Firm* — Dinsmore & Shohl LLP (57) ABSTRACT

A system for testing for contaminants in an assembly line grow pod includes a tray moving along a track arranged in an assembly line grow pod, a plurality of cells arranged on the tray and a contaminant sensor. Each cell supports seeds, plants, or both, and a selected cell includes side walls and a base that define a cavity. The contaminant sensor is arranged in the cavity of the selected cell. The contaminant sensor includes a sensing device and a control device. The sensing device directly senses a characteristic of a content present in association with the selected cell. The control device is coupled to the sensing device and operable to receive a signal from the sensing device. The control device may determine a likelihood of contamination based on the received signal.

19 Claims, 8 Drawing Sheets

(51) Int. Cl.
  *A01G 25/16*  (2006.01)
  *A01G 29/00*  (2006.01)
  *A01G 31/04*  (2006.01)
  *G01N 27/06*  (2006.01)
  *G01N 33/18*  (2006.01)

(52) U.S. Cl.
  CPC .......... *A01G 29/00* (2013.01); *A01G 31/042* (2013.01); *G01N 33/1826* (2013.01)

(56) References Cited

U.S. PATENT DOCUMENTS

| | | | | |
|---|---|---|---|---|
| 2007/0289207 A1* | 12/2007 | May | ......... | A01G 9/16 47/17 |
| 2017/0208757 A1* | 7/2017 | Valmont | ......... | B01F 5/0206 |
| 2018/0014486 A1* | 1/2018 | Creechley | ......... | A01G 7/045 |
| 2019/0000019 A1* | 1/2019 | Alexander | ......... | A01G 7/00 |

FOREIGN PATENT DOCUMENTS

| | | |
|---|---|---|
| JP | S59142396 A | 8/1984 |
| KR | 100985920 B1 | 10/2010 |
| KR | 101724380 B1 | 4/2017 |
| KR | 101725036 B1 | 4/2017 |
| WO | 2013/066254 A1 | 5/2013 |

OTHER PUBLICATIONS

Heidi Wollaeger, Calibrate you pH and EC meter in your greenhouse, Mar. 14, 2016, Michigan State University (Year: 2016).*
International Search Report and Written Opinion for PCT/US2018/032703 dated Sep. 25, 2018, 16 pages.
"Which Conductivity Sensor Suits Your Application?," https://www.coleparmer.com/tech-article/conductivity-sensors (accessed Mar. 28, 2018).
Kickstarter Campaign "AIRY, Bio-Active Air Filtering" Helge B. Knickmeier, et al., http://www.kickstarter.com/projects/airy/airy-bio-active-air-filtering (accessed Mar. 28, 2018).

* cited by examiner

SYSTEMS AND METHODS FOR TESTING FOR CONTAMINANTS IN AN ASSEMBLY LINE GROW POD

CROSS REFERENCE

This application claims the benefit of U.S. Provisional Application Ser. No. 62/519,403, filed on Jun. 14, 2017, which is incorporated by reference in its entirety.

TECHNICAL FIELD

Embodiments described herein generally relate to systems and methods for providing an assembly line grow pod and, more specifically, to systems and methods for testing contaminants in an assembly line grow pod when the assembly line grow pod is in use.

BACKGROUND

While crop growth technologies have advanced over the years, there are still many problems in the farming and crop industry today. As an example, while the United States currently has suitable farmland to adequately provide food for the U.S. population, other countries and future populations may not have enough farmland to provide the appropriate amount of food. Accordingly, there is a need to provide an organized plant grow pod system which facilitates a quick growing, small footprint, chemical free, low labor solution to growing microgreens and other plants for harvesting. At the same time, there is a need that the organized plant grow pod system may provide controlled environmental conditions (e.g., the timing and wavelength of light, pressure, temperature, watering, nutrients, molecular atmosphere, and/or other variables) to optimize plant growth and output, and ensure that plants ready for harvesting are not contaminated, thereby producing chemical free and environmentally clean plants.

SUMMARY

Systems and methods for testing for contaminants in an assembly line grow pod are described. One embodiment of the system includes a tray moving along a track arranged in an assembly line grow pod, a plurality of cells arranged on the tray and a contaminant sensor. Each cell supports seeds, plants, or both, and a selected cell includes side walls and a base that define a cavity. In some embodiments, the contaminant sensor is arranged in the cavity of the selected cell. The contaminant sensor includes a sensing device and a control device. The sensing device directly senses a characteristic of a content present in association with the selected cell. The control device is coupled to the sensing device and operable to receive a signal from the sensing device.

In another embodiment, an assembly line grow pod system includes a continuous track that holds one or more carts and a tray supported by the cart on the track and including a plurality of cells that support seeds, plants, or both, where a selected cell includes side walls and a base that define a cavity. The assembly line grow pod system further includes a contaminant sensor and a master controller. The contaminant sensor is arranged in the cavity of the selected cell and includes a sensing device and a control device. The sensing device directly senses various characteristics of contents of the selected cell. The control device is coupled to the sensing device and operable to receive a signal from the sensing device. The assembly line grow pod includes a master controller in communication with the contaminant sensor and including a processor and a memory storing instructions. The instructions, upon execution by the processor, perform (i) obtaining from the contaminant sensor initial information indicative of absence of contamination; (ii) establishing a baseline reading based on the initial information and storing the baseline reading in the memory; (iii) periodically obtaining new or updated information from the contaminant sensor; (iv) determining whether the new or updated information is different from the baseline reading; (v) upon determination of a difference, determining a presence of contamination; and (vi) upon determination of no difference, determining whether plants are ready for harvest.

In yet another embodiment, a method for testing for contaminants in an assembly line grow pod, includes (i) obtaining initial information indicative of absence of contamination from a first contaminant sensor with respect to a content present in a selected cell among a plurality of cells, wherein the cells are arranged on a tray and support seeds, plants, or both, wherein the selected cell includes side walls and a base that define a cavity; (ii) establishing a baseline reading based on the initial information; (iii) periodically obtaining new information from the first contaminant sensor with respect to the content present in the selected cell; (iv) determining whether the new information is different from the baseline reading; (v) upon determination of a difference, determining a presence of contamination within the selected cell; (vi) transmitting the presence of contamination to a plurality of components of the assembly line grow pod; and (vii) cleaning the selected cell and after cleaning, periodically obtaining the new information from the first contaminant sensor with respect to the content present in the selected cell.

These and additional features provided by the embodiments of the present disclosure will be more fully understood in view of the following detailed description, in conjunction with the drawings.

BRIEF DESCRIPTION OF THE DRAWINGS

The embodiments set forth in the drawings are illustrative and exemplary in nature and not intended to limit the disclosure. The following detailed description of the illustrative embodiments can be understood when read in conjunction with the following drawings, where like structure is indicated with like reference numerals and in which.

DETAILED DESCRIPTION

Embodiments disclosed herein include systems and methods for providing an assembly line grow pod. Some embodiments are configured with an assembly line of plants that follow a track that wraps around a first axis in a vertically upward direction and wraps around a second axis in vertically downward direction. These embodiments may utilize light emitting diode (LED) components for simulating a plurality of different light wavelengths for the plants to grow. Embodiments may also be configured to individually seed one or more sections of a tray on a cart, as well as provide customized water and nutrients to individual cells that hold those seeds. The customized water is monitored within the tray by one or more contaminant sensors to ensure that the seeds or plants within the tray are not subjected to contamination by contaminants, such as mold, bacteria, viruses, foreign particulate matter, decayed material, unnecessary and/or harmful minerals, and/or the like. The systems and methods for providing an assembly line grow pod incorporating the same will be described in more detail below.

Figure 1:
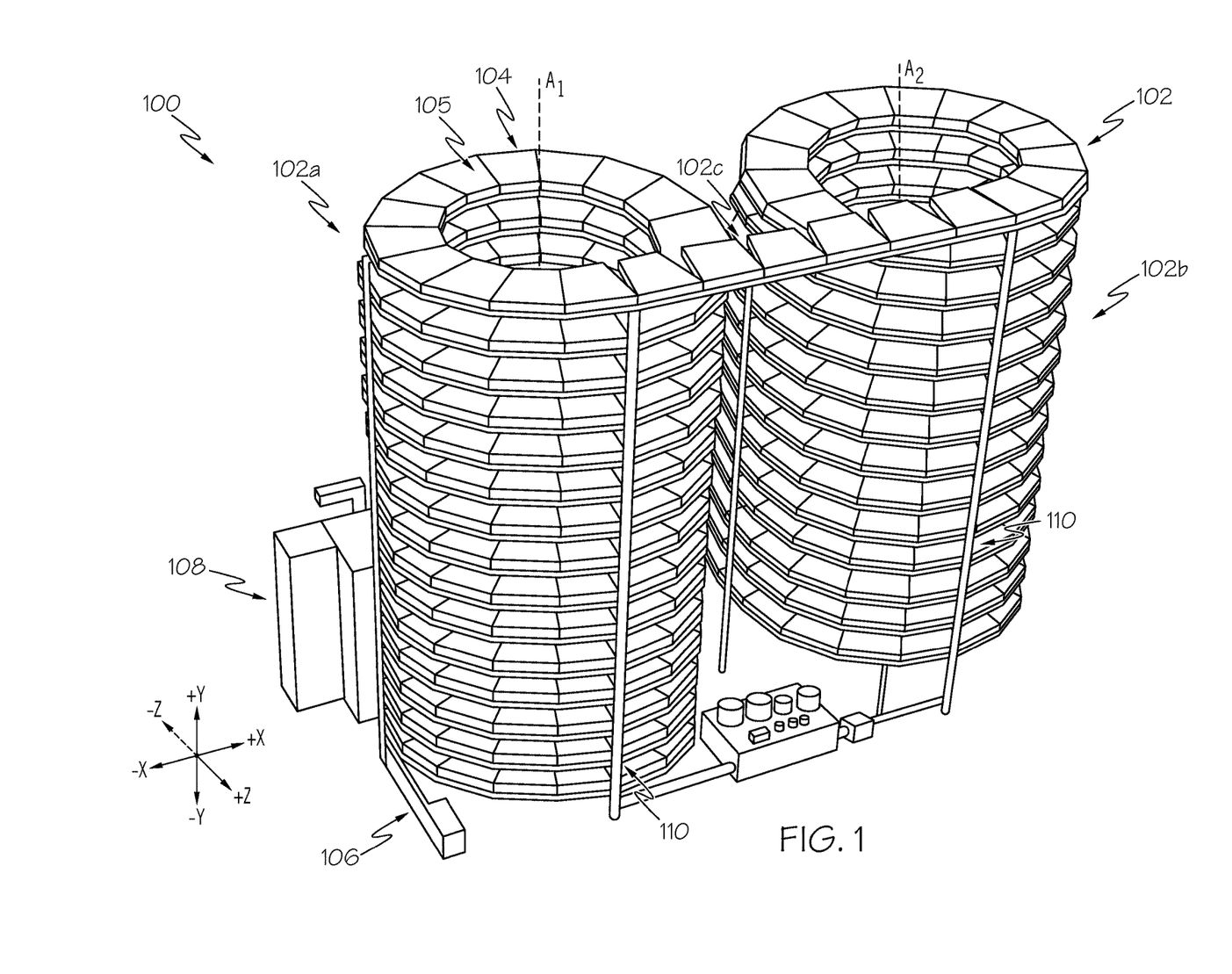
FIG. 1 depicts an illustrative assembly line grow pod according to one or more embodiments shown and described herein.

Referring now to the drawings, FIG. 1 depicts an assembly line grow pod 100, according to embodiments described herein. As illustrated, the assembly line grow pod 100 may include a track 102 that holds one or more carts 104, each cart having one or more trays 105 thereon. The track 102 may include an ascending portion 102a, a descending portion 102b, and a connection portion 102c. The track 102 may wrap around, in a counterclockwise direction in FIG. 1, a first axis such that the carts 104 ascend upward in a vertical direction. In other embodiments, clockwise or other configurations are available. The connection portion 102c may be relatively level (although this is not a requirement) and is utilized to transfer carts 104 (and the trays 105 thereon) to the descending portion 102b. The descending portion 102b may be wrapped around a second axis (again in a counterclockwise direction in FIG. 1) that is substantially parallel to the first axis, such that the carts 104 may be returned closer to ground level.

While not explicitly illustrated in FIG. 1, the assembly line grow pod 100 may also include a plurality of lighting devices, such as light emitting diodes (LEDs). The lighting devices may be disposed on the track 102 opposite the carts 104, such that the lighting devices direct light waves to the carts 104 on the portion the track 102 directly below. In some embodiments, the lighting devices are configured to create a plurality of different colors and/or wavelengths of light, depending on the application, the type of plant being grown, and/or other factors. While in some embodiments, LEDs are utilized for this purpose, this is not a requirement. Any lighting device that produces low heat and provides the desired functionality may be utilized.

Also depicted in FIG. 1 is a master controller 106. The master controller 106 may include a computing device and various control modules for controlling various components of the assembly line grow pod 100 such as a nutrient dosing control module, a water distribution control module, etc. As an example, control modules for controlling a water distribution control module, a nutrient distribution control module, an air distribution control module, etc. may be included as part of the master controller 106 which may provide a modular control interface. The modular control interface of the master controller 106 enables removal, replacement, upgrade and expansion of each control module without changing or affecting the operations of other control modules, or shutting down the master controller 106 or other components of the assembly line grow pod 100.

Figure 2:
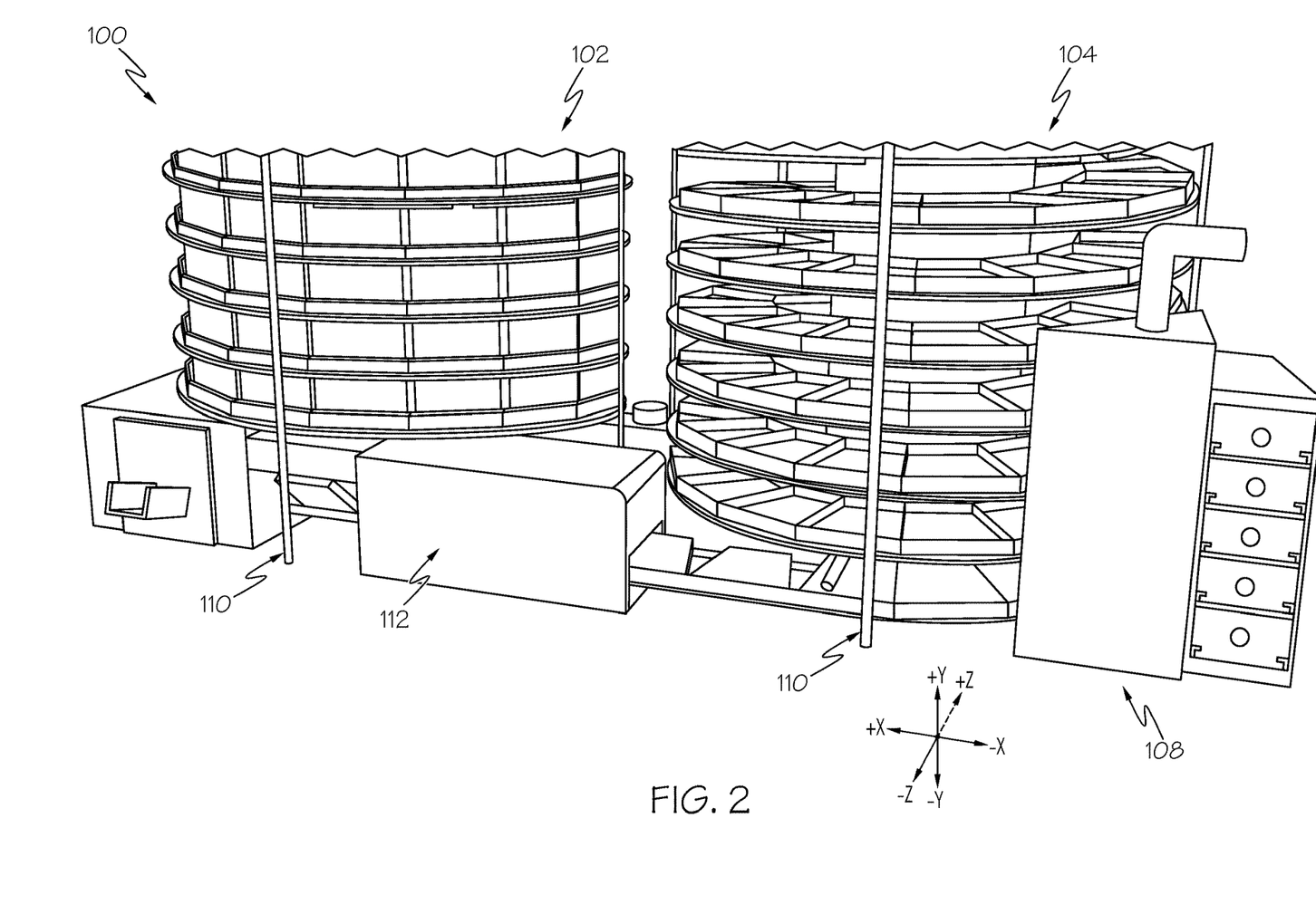
FIG. 2 schematically depicts a rear perspective view of a portion of an illustrative assembly line grow pod having a seeder component.
Figure 3:
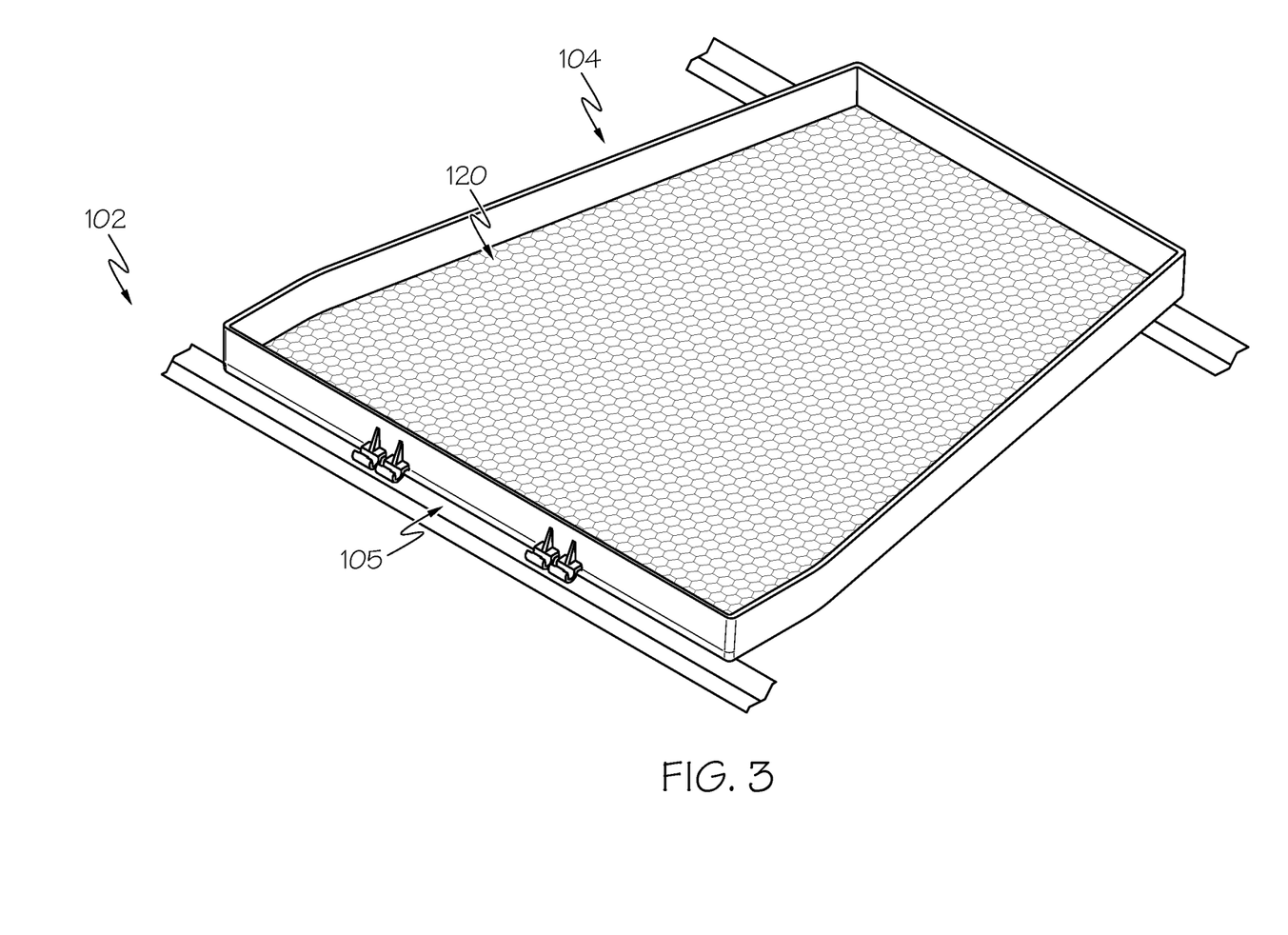
FIG. 3 depicts an illustrative tray supported by a cart on a track within an assembly line grow pod according to one or more embodiments shown and described herein.

Coupled to the master controller 106 is a seeder component 108, as shown in FIG. 2. The seeder component 108 may be configured to seed each tray 105 on the one or more carts 104 as the carts 104 pass the seeder in the assembly line. In some embodiments, each cart 104 may include a single section tray for receiving a plurality of seeds. In other embodiments, a multiple section tray may be used to receive individual seeds in each section (or cell), as shown in FIG. 3 and will be discussed more in detail below. In the embodiments with the single section tray, the seeder component 108 may detect presence of the respective cart 104 and may begin laying seed across an area of the single section tray. The seed may be laid out according to a desired depth of seed, a desired number of seeds, a desired surface area of seeds, and/or according to other criteria. In some embodiments, the seeds may be pre-treated with nutrients and/or anti-buoyancy agents (such as water) as these embodiments may not utilize soil to grow the seeds and thus might need to be submerged.

In the embodiments where the multiple section tray is utilized with one or more of the carts 104, the seeder component 108 may be configured to individually insert seeds into one or more of the sections of the tray. Again, the seeds may be distributed on the tray (or into individual cells) according to a desired number of seeds, a desired area the seeds should cover, a desired depth of seeds, etc.

The watering control module may be coupled to one or more water lines 110, which distribute water and/or nutrients to one or more trays at predetermined areas of the assembly line grow pod 100. In some embodiments, seeds may be sprayed to reduce buoyancy and then flooded. Additionally, water usage and consumption may be monitored utilizing various sensors coupled to each tray 105, such that at subsequent watering stations, this data may be utilized to determine an amount of water to apply to a seed at that time.

It should be understood that while the embodiment of FIG. 1 depicts an assembly line grow pod 100 that wraps around a plurality of axes, this is merely one example. FIGS. 1 and 2 illustrate a two towers structure of the assembly line grow pod 100, but in other embodiments, a four towers structure is available. In addition, any configuration of assembly line or stationary grow pod may be utilized for performing the functionality described herein.

FIG. 3 depicts a detailed view of a tray 105 supported by the cart 104 on the track. As shown in FIG. 3, the tray 105 includes a plurality of cells 120 therein that support the seeds and/or plants. That is, each cell 120 has an open end in which the seed, water, and nutrients are deposited. The cells 120 can be arranged in any manner on the tray 105, and such an arrangement is not limited by the present disclosure. As an example, some embodiments may be configured to receive individually placed seeds into one or more of the cells 120. Some embodiments may be configured for a plurality of seeds to be laid across the tray 105, allowing the seeds to fall into the cells 120. In some embodiments, the seeds may be laid such that some seeds reside inside of the cells 120, while others lay on top of those seeds in one or more layers of seeds.

Figure 4:
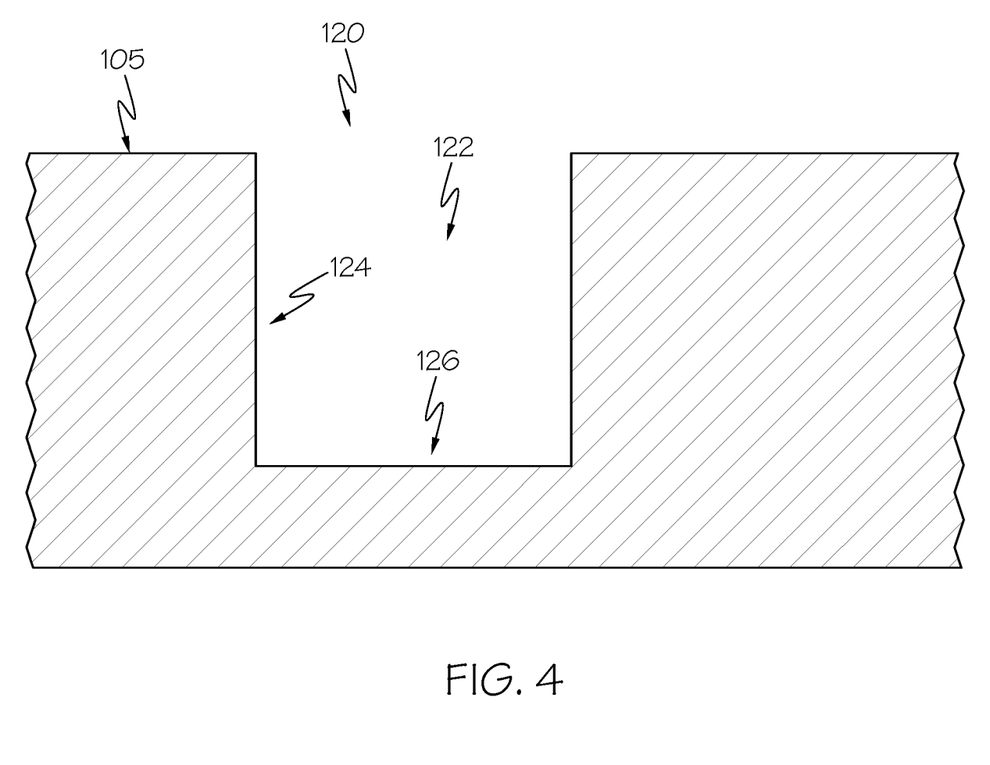
FIG. 4 depicts a cross sectional and enlarged view of an illustrative cell within a tray according to one or more embodiments shown and described herein.

FIG. 4 depicts a cross-sectional side view and an enlarged view of an illustrative cell 120 within the tray 105. The cell 120 has one or more side walls 124 and a base 126 that defines a cavity 122 in which the seeds can be deposited. The shape and size of each cell 120 is not limited by this disclosure, and may generally be any shape and/or size suitable for holding a seed, water, and/or nutrients therein, as well as any plant that sprouts from the seed before it is harvested. It should be understood that certain cells 120 may be shaped and/or sized for particular types of seeds and/or plants held therein.

Figure 5:
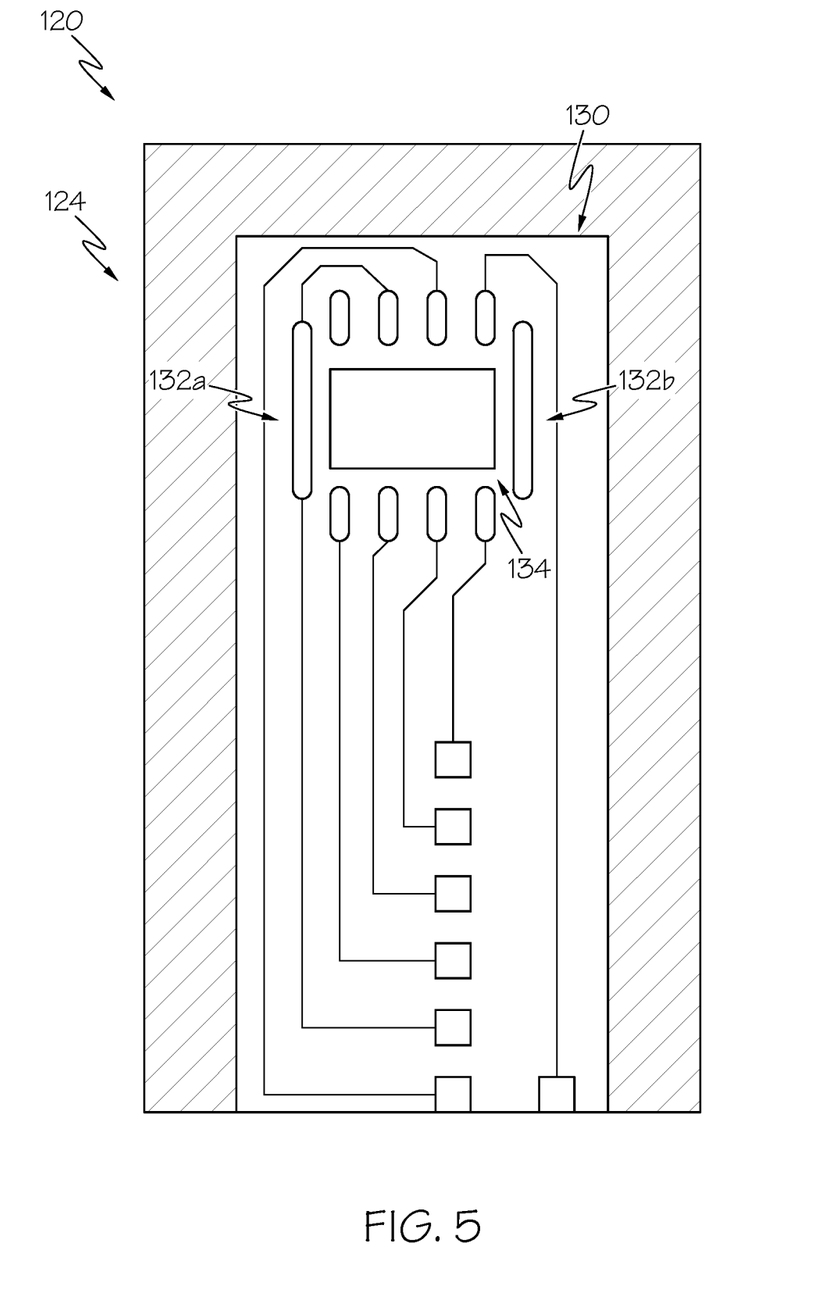
FIG. 5 depicts an illustrative contaminant sensor coupled to a side wall of a cell within a tray according to one or more embodiments shown and described herein.

At least a portion of the cells 120 may be coupled to a device that measures various characteristics of the contents of the cell 120 such that a determination can be made as to whether the cell contains contaminants therein, such as the contaminants listed hereinabove. Accordingly, one of the side walls 124 of the cell 120 may be coupled to (or embedded with) a contaminant sensor 130, as depicted in FIG. 5. The contaminant sensor 130 may be a circuit board or the like that contains various components, traces, and/or the like for testing for one or more indicators of a presence of a contaminant within the cell 120.

In various embodiments, the contaminant sensor 130 may include a plurality of probes 132*a*-132*b* (collectively, 132). The plurality of probes 132 may be arranged such that each of the plurality of probes 132 contacts the fluid in the cell, as described in greater detail herein. Each of the plurality of probes 132 may be constructed of an electrically conductive material, and at least one of the plurality of probes 132 is electrically coupled to a power source. Each of the plurality of probes 132 may further be coupled to a control device 134 that is configured to receive one or more signals from at least one of the plurality of probes 132. In some embodiments, the control device 134 determines a likelihood of a contaminant being present in the fluid based on the received one or more signals.

Figure 6:
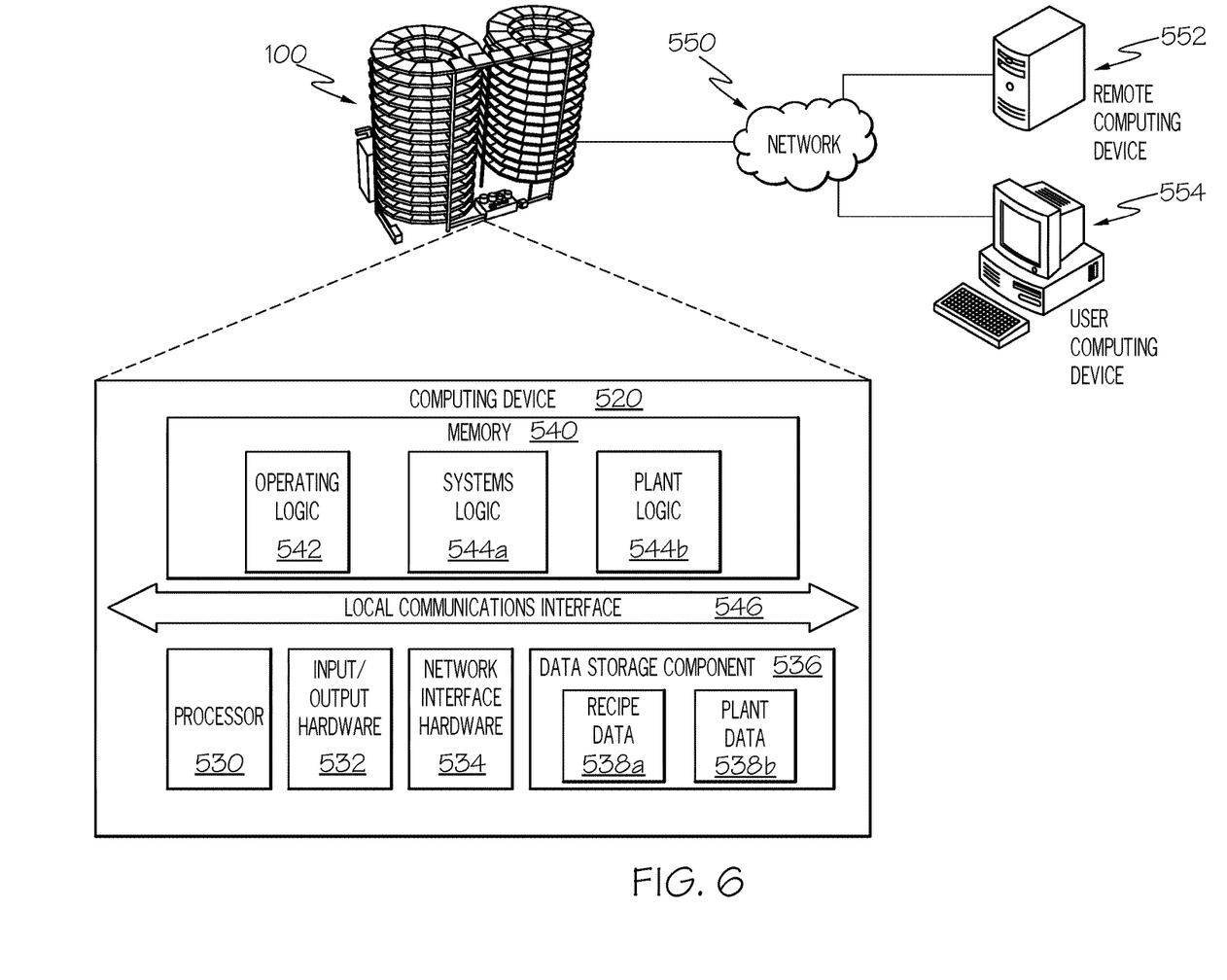
FIG. 6 depicts an illustrative computing network and various computer hardware components within a computing device of an assembly line grow pod according to one or more embodiments shown and described herein.

In some embodiments, the control device 134 may only act as a relay between the plurality of probes 132 and an external device such as the master controller 106 (FIG. 1) or a component thereof, as shown in FIG. 6. That is, the control device 134 may not make a determination of a likelihood of a contaminant being present in the fluid. Instead, the control device 134 may transmit one or more signals to an external device, such as the master controller 106 (FIG. 1) or a component thereof.

In some embodiments, the fluid in use may exhibit a particular conductivity when an electrical charge is supplied thereto. As such, when the fluid is present within the cell 120, a first probe 132*a* of the plurality of probes 132 may provide an electrical charge while a second probe 132*b* of the plurality of probes, which is spaced a distance from the first probe 132*a*, measures the amount of charge that is detected. The measured charge at the second probe 132*b* is used to determine the conductivity of the fluid. For example, the second probe 132*b* may transmit a signal to the control device 134, where the signal corresponds to the amount of charge that is detected. The control device 134 then determines the conductivity of the fluid based on a set amount of charge that was supplied by the first probe 132*a*. Calculation of the conductivity based on these parameters should generally be understood in the pertinent art and is not described in further detail herein. To determine whether a contaminant is present within the fluid in the cell 120, the conductivity of the fluid may be measured as soon as the fluid is placed within the cell 120. The initial measurement made immediately after the fluid is placed is used to establish a baseline reading, as it may be assumed that the fluid at first placement is uncontaminated. The conductivity of the fluid may then be periodically measured at various intervals after the baseline reading has been established. Any increase in conductivity of the fluid may be indicative of a presence of a contaminant. The control device 134 may transmit a signal to an external device (e.g., the master controller 106 (FIG. 1)) to indicate the potential of contamination, or a lack of contamination.

It should be understood that the various components of the contaminant sensor 130 described herein are merely illustrative, and additional or alternative components may also be used to test for the presence of contaminants within the cell 120. For example, the contaminant sensor 130 may be configured to test a pH of the fluid in the cell 120, test an impedance of the fluid in the cell 120, and/or the like. In another example, the contaminant sensor may contain one or more optical sensors that sense various optical features of the fluid in the cell 120, which may further be used to determine whether contaminants are present in the cell 120. In some embodiments, additional sensing other than conductivity sensing may be used for the purposes of verifying the presence of contaminants, distinguishing between different types of contaminants (e.g., mold vs. decaying matter), and/or the like.

In other embodiments, the contaminant sensor 130 may further be used for other purposes in addition to sensing for contaminants within the cell. For example, the contaminant sensor 130 may measure a concentration of nutrients within the cell 120, may measure a color of the plant within the cell, which may be used to determine if the plant is healthy, may measure for the presence and/or volume of fluid in the cell 120, and/or the like. It should be understood that these additional capabilities of the contaminant sensor 130 are merely illustrative, and other capabilities not mentioned above are contemplated and within the scope of the present disclosure.

If contamination in the cell 120 may be determined by the control device 134, or the master controller 106 (FIG. 1), the master controller 106 may perform operations to correct the contamination issues. If and after the contamination issues are corrected, the master controller 106 determines whether plants are ready for harvest and proceed to harvesting plants, as will be further discussed in connection with FIG. 7. With respect to seeds, the master controller 106 may flag one or more cells 120 that have been found to have the contamination issues and restrict using such cells 120. In some embodiments, the master controller 106 transmits and outputs a notification message or an alert message notifying a user such that the flagged cells 120 may be excluded from future seeding. In other embodiments, the master controller 106 may instruct and control a seeding mechanism or a seeding device such as a robot arm (not shown) which performs automatic seeding, such that the robot arm may not despot seeds in the flagged cells 120.

In some embodiments, the flagged cells 120 may be filled with a material that prevents seeds from entering into the affected cells. Alternatively, or additionally, the flagged cells 120 may be completely closed or sealed to avoid any accidental depositing of seeds. In other embodiments, the flagged cells 120 may be subject to a cleaning process and upon determination that the contamination issues have been corrected as a result of the cleaning process, the master controller 106 may remove the flagged status of the cells 120 and put the cleaned cells 120 back to use.

While FIG. 5 depicts a single contaminant sensor 130 located in a single cell 120, the present disclosure is not limited. For example, a single contaminant sensor 130 may be used for all of the cells 120 in a tray, a group of cells 120 in a tray, or the like. In another example, a single contaminant sensor 130 communicatively coupled to a plurality of probes 132 in each of a plurality of cells 120 may be used. Other combinations are contemplated and are within the scope of the present disclosure.

FIG. 6 depicts various internal components of one or more control systems within the assembly line grow pod 100 that may utilize data from the contaminant sensor 130 (FIG. 5) to determine a presence of a contaminant in a cell (or a likelihood of a presence), determine one or more actions in response to the determined presence, and transmit one or more signals in response to the determined actions. In some embodiments, such internal components may generally be within a computing environment. As illustrated, the assembly line grow pod 100 (or a control system thereof) may include a computing device 520. In some embodiments, the master controller 106 as shown in FIG. 1 may be implemented with the computing device 520. The computing device 520 includes a processor 530, input/output hardware 532, the network interface hardware 534, a data storage component 536 (which stores systems data 538a, plant data 538b, and/or other data), and the memory component 540. The memory component 540 may be configured as volatile and/or nonvolatile memory and as such, may include random access memory (including SRAM, DRAM, and/or other types of RAM), flash memory, secure digital (SD) memory, registers, compact discs (CD), digital versatile discs (DVD), and/or other types of non-transitory computer-readable mediums. Depending on the particular embodiment, these non-transitory computer-readable mediums may reside within the computing device 520 and/or external to the computing device 520.

The memory component 540 may store operating logic 542, systems logic 544a, and plant logic 544b. The systems logic 544a and the plant logic 544b may each include a plurality of different pieces of logic, each of which may be embodied as a computer program, firmware, and/or hardware, as an example. The systems logic 544a may monitor and control operations of one or more of the fluid control component, pumps, water lines, and/or the like, as well as control each contaminant sensor 130 (FIG. 5) or send/receive signals from each contaminant sensor 130. The plant logic 544b may be configured to determine and/or receive a recipe for plant growth and may facilitate implementation of the recipe via the systems logic 544a. In some embodiments, the recipe for plant growth may dictate the timing and wavelength of light, pressure, temperature, watering, nutrients, molecular atmosphere, and/or other variables the optimize plant growth and output, and then monitor the fluid in the cells to ensure that the cells are not contaminated, thereby ensuring optimal plant growth. The plant logic 544b may further be configured to determine steps for reducing/eliminating contaminants within a cell, as well as implementation of such steps (e.g., disposing of the material within the cells, cleaning the cells, supplying certain additives to combat the contaminants, etc.).

The operating logic 542 may include an operating system and/or other software for managing components of the computing device 520. As also discussed above, systems logic 544a and the plant logic 544b may reside in the memory component 540 and may be configured to perform the functionality, as described herein.

It should be understood that while the components in FIG. 6 are illustrated as residing within the computing device 520, this is merely an example. In some embodiments, one or more of the components may reside external to the computing device 520. It should also be understood that, while the computing device 520 is illustrated as a single device, this is also merely an example. In some embodiments, the systems logic 544a and the plant logic 544b may reside on different computing devices. As an example, one or more of the functionalities and/or components described herein may be provided by a user computing device and/or a remote computing device.

Additionally, while the computing device 520 is illustrated with the systems logic 544a and the plant logic 544b as separate logical components, this is also an example. In some embodiments, a single piece of logic (and/or or several linked modules) may cause the computing device 520 to provide the described functionality.

A local interface 546 is also included in FIG. 6 and may be implemented as a bus or other communication interface to facilitate communication among the components of the computing device 520. The processor 530 may include any processing component operable to receive and execute instructions (such as from a data storage component 536 and/or the memory component 540). The input/output hardware 532 may include and/or be configured to interface with microphones, speakers, a display, and/or other hardware.

The network interface hardware 534 may include and/or be configured for communicating with any wired or wireless networking hardware, including an antenna, a modem, LAN port, wireless fidelity (Wi-Fi) card, WiMax card, ZigBee card, Bluetooth chip, USB card, mobile communications hardware, and/or other hardware for communicating with other networks and/or devices. From this connection, communication may be facilitated between the computing device 520 and other devices external to the computing device, such as each contaminant sensor 130 (FIG. 4).

Additionally, the assembly line grow pod 100 is coupled to a network 550. The network 550 may include the internet or other wide area network, a local network, such as a local area network, a near field network, such as Bluetooth or a near field communication (NFC) network. The network 550 is also coupled to a user computing device 552 and/or a remote computing device 554. The user computing device 552 may include a personal computer, laptop, mobile device, tablet, server, etc. and may be utilized as an interface with a user. As an example, a user may send a plant recipe to the computing device 520 for implementation by the assembly line grow pod 100. Another example may include the assembly line grow pod 100 sending notifications to a user of the user computing device 552 (e.g., to notify the user of the presence of contaminants). Such notifications may enable a user to take necessary measures to remove or correct contaminants prior to harvesting, dispose of plants that have been found to have the contamination issues, etc.

Similarly, the remote computing device 554 may include a server, personal computer, tablet, mobile device, etc. and may be utilized for machine to machine communications. As an example, if the assembly line grow pod 100 determines a type of seed being used (and/or other information, such as ambient conditions), the computing device 520 may communicate with the remote computing device 554 to retrieve a previously stored recipe for those conditions. As such, some embodiments may utilize an application program interface (API) to facilitate this or other computer-to-computer communications.

Figure 7:
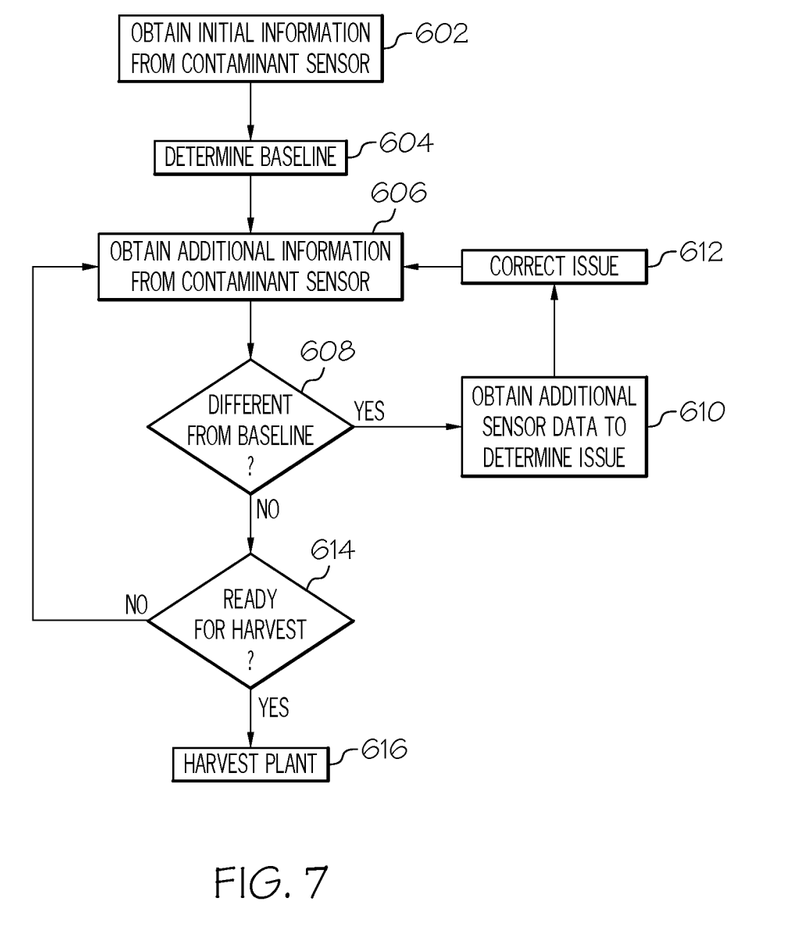
FIG. 7 depicts a flow diagram of an illustrative method of utilizing a contaminant sensor in an assembly line grow pod according to one or more embodiments shown and described herein.

FIG. 7 depicts a flow diagram for utilizing a contaminant sensor an assembly line grow pod 100, according to embodiments described herein. As illustrated in block 602, initial information is obtained from each contaminant sensor such that a baseline reading can be established in block 604. In some embodiments, the initial information is obtained by measuring the conductivity of the fluid as soon as the fluid is placed within the cell 120, assuming that the fluid at first placement is uncontaminated. This initial information such as the initial conductivity of the fluid will be used to establish a baseline reading. Once a baseline reading has been established, the contaminant sensor may periodically obtain new information or new data in block 606. For example, the conductivity of the fluid may then be measured at various intervals after the baseline reading has been established. This may occur continuously or at particular time intervals by directing the first probe to send an electrical charge and directing the second probe to receive an electrical charge so that the conductivity of the fluid can be determined. A determination is made in block 608 as to whether the new reading differs from the baseline reading. By way of example, when the conductivity of the fluid is continuously periodically measured, any increase in conductivity of the fluid may be indicative of a presence of a contaminant.

If a difference exists, additional sensor data may optionally be obtained to determine an issue (e.g., a presence of a particular contaminant) in block 610. In some embodiments, optical sensors may be used to sense various optical features of the fluid in the cell 120, which may further be used to determine whether contaminants are present in the cell 120. Additionally, or alternatively, additional sensors that can detect other than conductivity sensing, may be used to verify the presence of contaminants and distinguishing between different types of contaminants (e.g., mold vs. decaying matter). Instructions may be provided to various components to correct the issue in block 612. In some embodiments, the instructions may be provided by the master controller 106 to the seeder 108, controllers for controlling operations of the carts 105, the tray 104, a sanitizer 112, etc. in FIG. 2. Correction of the contamination issues will be discussed more in detail in connection with FIG. 8 below. The process may return to block 606 if the correction does not involve destroying/disposing of the seeds/plants. If no difference exists between the baseline and new sensor data in block 608, a determination may be made in block 614 as to whether the plant is ready for harvest. If the plant is not ready for harvest, the process may return to block 606 after a period of time has elapsed to continue to monitor for potential contaminants in the cell. If the plant is ready for harvesting, it may be harvested in block 616.

Figure 8:
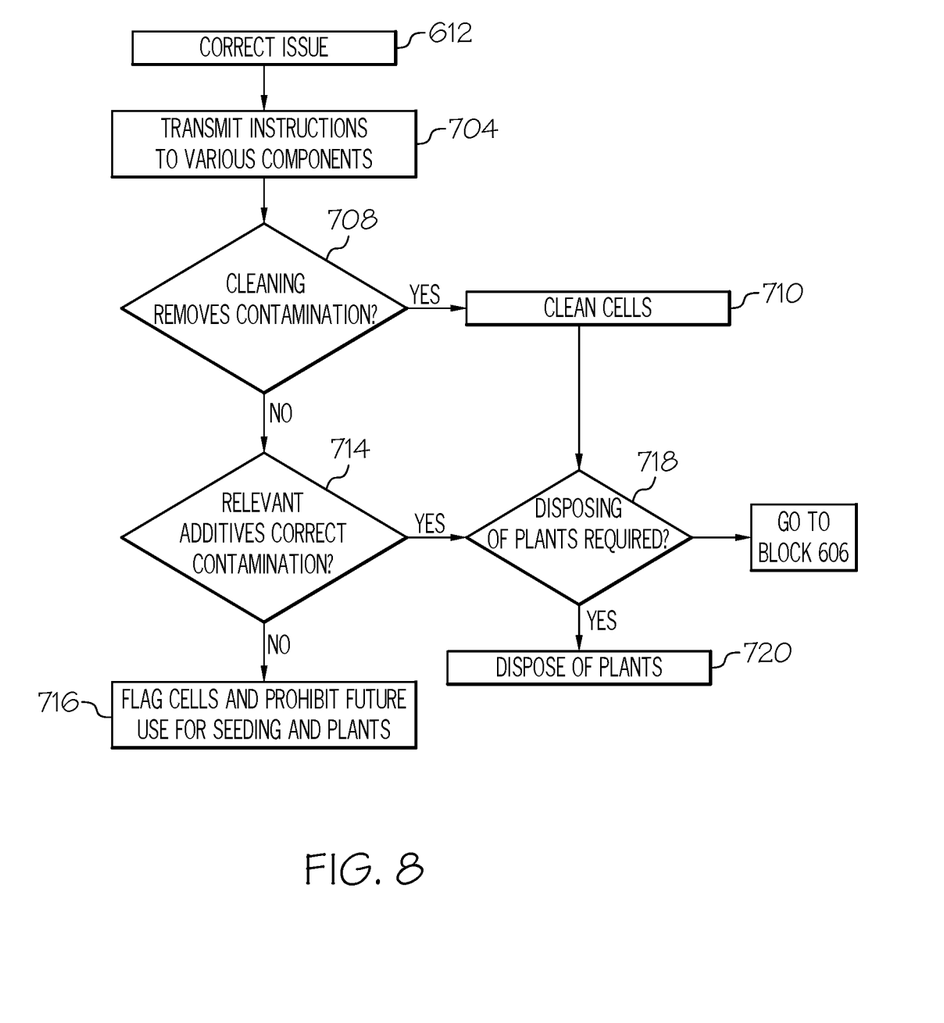
FIG. 8 depicts a flow diagram of an illustrative method of correcting contamination issues in an assembly line grow pod according to one or more embodiments shown and described herein.

FIG. 8 depicts a flow diagram for correcting the contamination issues detected and/or determined by the contaminant sensor for the assembly line grow pod 100, according to embodiments described herein. As discussed above in connection with FIG. 7, once the contamination issues may be determined (block 608) and confirmed with the additional sensor data (block 610), then correcting the contamination issues follows (block 612). Instructions relating to correcting the contamination issues are sent to various components of the assembly line grow pod 100 (block 704). In some embodiments, those components may include the seeder 108, the sanitizer 112, the carts 105, the tray 104, etc. For instance, the seeder 108 may include automatic seeding mechanism implemented with a robot arm and be instructed not to deposit any seed in particular cells that have been identified to have the contamination issue. For this purpose, the master controller 106 may recognize, flag and record the particular cells on a particular tray 104 moving on a particular cart 105 and notify the relevant components of the contamination issues. Based on the flagged cell information from the master controller 106, the seeder 108 may instruct the robot arm (not shown) not to deposit seeds in the flagged cell(s). Based on the flagged cell information, the sanitizer 112 receives the particular cart 105 having the flagged cell(s) on the tray 104 and perform sanitizing and cleaning process of the flagged cell(s).

The master controller 106 further determines whether cleaning the flagged cell(s) may remove contaminants and resolve the contamination issues (block 708). In some instances, the contaminants may be resistant to cleaning by water and require more treatment. If removing the contaminants requires more than cleaning the flagged cell(s), it is determined whether adding relevant additives to the cells may remove contaminants (block 714). If cleaning and additives do not remove contaminants, the master controller 106 may record the flagged cells as contaminated cells and record and send out a notification or alert message to the relevant components and/or a user computing device. The notification or alert message includes a notification that the particular cells will be prohibited from a potential use. The particular cells and/or the entire tray may be closed or sealed. If the rest of the tray may be still in use, except for the particular cells, a material may be used to fill in the particular cells to prevent any seed from entering into the affected cells.

If cleaning and/or adding additives may remove the contamination issue, the master controller 106 may determine whether disposing of any plant in the affected cells is needed (block 718). If disposing of plants is not needed, then the process goes back to checking the contamination state of the affected cells (block 606). Otherwise, the master processor may send out a notification or alert message to the relevant components and/or a user computing device that indicates or requires disposal of plants in the affected cells (block 720).

As illustrated above, various embodiments for providing an assembly line grow pod are disclosed. These embodiments create a quick growing, small footprint, chemical free, low labor solution to growing microgreens and other plants for harvesting. These embodiments may create recipes and/or receive recipes that dictate the timing and wavelength of light, pressure, temperature, watering, nutrients, molecular atmosphere, and/or other variables the optimize plant growth and output, and then monitor the fluid in the cells to ensure that the cells are not contaminated, thereby ensuring optimal and chemical free plant growth and plant production.

As illustrated above, various embodiments of systems and methods for testing a contaminant for use with an assembly line grow pod are disclosed. The embodiments may use a contaminant sensor which can detect information indicative of potential contamination, or a lack of contamination. The contaminant sensor is arranged in one or more of a plurality of cells arranged on a tray which supports plants, seeds, or both. The contaminant sensor may be in direct contact with a content present in the cells and transmit relevant information. The contaminant sensor may include a control device which determines potential contamination within the relevant cell(s). Alternatively, or additionally, the contaminant sensor may be communicatively coupled to a master controller that controls and monitors operations of the contaminant sensor. The master controller also controls and monitors operations of various components of the assembly line grow pod. The master controller may determine potential contamination or a lack of contamination based on the information received from the contaminant sensor.

The contaminant sensor may have additional capability of detecting information such as color of a plant, nutrient concentration, fluid volume, and/or presence of fluid in relevant cell(s). As the contaminant sensor may be arranged in direct contact with one or more cells, the contaminant sensor can effectively detect relevant information relating to the growth states and conditions of plants, seeds, etc. In addition, the contaminant sensor may not occupy a large space and be installed in a cavity formed in each cell, space and cost saving may be obtained in the assembly line grow pod.

The method for testing a contaminant for use with the assembly line grow pod include the steps of (i) obtaining from the contaminant sensor initial information indicative of absence of contamination; (ii) establishing a baseline reading based on the initial information and storing the baseline reading in the memory; (iii) periodically obtaining new information from the contaminant sensor; (iv) determining whether the new information is different from the baseline reading; (v) upon determination of a difference, determining a presence of contamination; and (vi) upon determination of no difference, determining whether plants are ready for harvest. Prior to harvest, any potential contamination may be determined which ensures that plants are ready for harvest. In addition, upon determination of any potential contamination, a particular contaminant may be identified with another sensor and relevant steps to correct or resolve the contamination may be performed. For instance, cleaning the cell(s) showing a sign of contamination may be cleaned, plants in those cell(s) can be disposed of without affecting the rest of crop, and/or relevant additives may be added to correct contamination. It is possible to ensure harvesting of healthy and productive crop by periodically monitoring contamination states of cells on a tray with a contaminant sensor. Furthermore, determination of contamination may be automated by comparing the baseline reading indicative of no contamination and updated reading and frequent and automated contamination check is possible.

If it is determined that contaminated cell(s) may not completely correct or resolve the contamination issues, then such cell(s) may be closed or shut off for any future use. Plants in those cells may be disposed of and do not proceed to harvesting. Moreover, such cell(s) may be closed or sealed with a material that restricts or blocks any seed from entering. A seeder component is notified and instructed to program an automatic seeding device to avoid depositing of seed in the affected cell(s). A sanitizer component is notified and instructed to program to perform cleaning and sanitizing processes on the tray having the affected cell(s).

While particular embodiments and aspects of the present disclosure have been illustrated and described herein, various other changes and modifications can be made without departing from the spirit and scope of the disclosure. Moreover, although various aspects have been described herein, such aspects need not be utilized in combination. Accordingly, it is therefore intended that the appended claims cover all such changes and modifications that are within the scope of the embodiments shown and described herein.

It should now be understood that embodiments disclosed herein include systems, methods, and non-transitory computer-readable mediums for testing a contaminant for use in an assembly line grow pod. It should also be understood that these embodiments are merely exemplary and are not intended to limit the scope of this disclosure.

What is claimed is:

1. A system for testing for contaminants in an assembly line grow pod, comprising:
   a master controller;
   a tray moving along a track arranged in an assembly line grow pod;
   a plurality of cells arranged on the tray and supporting seeds, plants, or both, wherein a selected cell includes side walls and a base that define a cavity; and
   a contaminant sensor arranged in the cavity of the selected cell, comprising:
      a sensing device for directly sensing a characteristic of a content present in association with the selected cell; and
      a control device coupled to the sensing device and operable to receive a signal indicative of the characteristic of the content from the sensing device, and transmit the signal to the master controller,
   wherein the control device of the contaminant sensor forgoes making a determination of a likelihood of a contaminant being present in the selected cell, the master controller then makes the determination of the likelihood of the contaminant being present in the selected cell based on the signal received from the control device of the contaminant sensor.

2. The system of claim 1, wherein the contaminant sensor includes a circuit board that includes components for detecting a presence of a contaminant within the selected cell.

3. The system of claim 1, wherein the sensing device further includes a plurality of probes made from an electrically conductive material and at least one of the plurality of probes is electrically coupled to a power source.

4. The system of claim 3, wherein the control device is configured to receive one or more signals from at least one of the plurality of probes and determine a likelihood of a contaminant being present in the selected cell based on the received signals.

5. The system of claim 3, wherein the control device is configured to receive one or more signals from at least one of the plurality of probes and transmit the signals to the master controller as a relay between the plurality of probes and the master controller.

6. The system of claim 3, wherein the plurality of probes include a first probe and a second probe spaced apart from the first probe and wherein the first probe provides an electrical charge while the second probe measures an amount of charge that has been detected.

7. The system of claim 6, wherein the amount of charge measured at the second probe is used to determine conductivity of a fluid and the second probe transmits a signal to the control device, wherein the signal corresponds to an amount of charge that is detected.

8. An assembly line grow pod system, comprising:
   a continuous track that holds one or more carts;
   a tray supported by the one or more carts moving on the continuous track and including a plurality of cells that support seeds, plants, or both, where a selected cell includes side walls and a base that define a cavity;
   a contaminant sensor arranged in the cavity of the selected cell, comprising;
      a sensing device for directly sensing a characteristic of a content of the selected cell; and
      a control device coupled to the sensing device and operable to receive a signal from the sensing device;
   a master controller in communication with the contaminant sensor and including a processor and a memory storing instructions, wherein the instructions, upon execution by the processor, perform operations comprising:
obtaining from the contaminant sensor initial information indicative of absence of contamination;
establishing a baseline reading based on the initial information and storing the baseline reading in memory;
obtaining updated information from the contaminant sensor;
determining whether updated information is different from the baseline reading;
upon determination of a difference, determining a presence of contamination; and
upon determination of no difference, determining whether plants are ready for harvest,
wherein the control device of the contaminant device forgoes making a determination of the presence of contamination and transmits the signal to the master controller, the master controller making the determination of the presence of contamination in the selected cell.

9. The assembly line grow pod system of claim 8, wherein the instructions, upon execution by the processor, further perform:
obtaining another set of data from an optical sensor to identify a particular contaminant.

10. The assembly line grow pod system of claim 9, wherein the instructions, upon execution by the processor, further perform one of the following:
upon determination of the presence of contamination,
disposing of the particular contaminant,
cleaning the selected cell, and
supplying additives to correct the particular contaminant.

11. The assembly line grow pod system of claim 8, wherein the sensing device further includes a plurality of probes made from an electrically conductive material and at least one of the plurality of probes is electrically coupled to a power source.

12. The assembly line grow pod system of claim 11, wherein the control device is configured to receive one or more signals from at least one of the plurality of probes and transmit the signals to the master controller as a relay between the plurality of probes and the master controller.

13. The assembly line grow pod system of claim 11, wherein the control device of the contaminant sensor stops sensing whether a contaminant is present in the selected cell, while the control device operates as a relay between the plurality of probes and the master controller.

14. The assembly line grow pod system of claim 8, wherein the master controller monitors and controls operations of the contaminant sensor.

15. A method for testing for contaminants in an assembly line grow pod, comprising:
obtaining initial information indicative of absence of contamination from a control device of a first contaminant sensor with respect to a content present in a selected cell among a plurality of cells, wherein the cells are arranged on a tray and support seeds, plants, or both, wherein the selected cell includes side walls and a base that define a cavity;
establishing a baseline reading based on the initial information;
periodically obtaining new information from the first contaminant sensor with respect to the content present in the selected cell;
determining whether the new information is different from the baseline reading;
upon determination of no difference, determining whether plants are ready for harvest;
upon determination of a difference, determining a presence of contamination within the selected cell;
transmitting the presence of contamination to a plurality of components of the assembly line grow pod; and
cleaning the selected cell and after cleaning, periodically obtaining the new information from the first contaminant sensor with respect to the content present in the selected cell,
wherein the control device of the contaminant sensor forgoes making a determination of a the presence of contamination in the selected cell, but instead sends the initial information and the new information to a master controller for making the determination of the presence of contamination in the selected cell.

16. The method of claim 15, further comprising arranging one or more sensors in connection with the selected cell and measuring with the sensors:
a concentration of nutrients, a color of a plant within the selected cell, presence and volume of fluid in the selected cell, a pH of a fluid in the selected cell, an impedance of the fluid in the selected cell, or a combination thereof.

17. The method of claim 15, wherein transmitting the presence of contamination further comprises transmitting the presence of contamination to a seeder component such that the seeder component stops depositing seeds in the selected cell.

18. The method of claim 15, further comprising: upon determination of the presence of contamination within the selected cell, applying relevant additives to the selected cell to remove the contamination.

19. The method of claim 15, wherein transmitting the presence of contamination further comprises transmitting the presence of contamination to a sanitizer component such that the sanitizer component sanitizes the selected cell and the tray where the selected cell is arranged.

* * * * *